(12) United States Patent
Carlebach

(10) Patent No.: US 6,428,483 B1
(45) Date of Patent: Aug. 6, 2002

(54) WAVEFORM INTERPRETER FOR RESPIRATORY ANALYSIS

(75) Inventor: Ephraim Carlebach, Raanana (IL)

(73) Assignee: Oridion Medical 1987, Ltd., Jerusalem (IL)

(*) Notice: Subject to any disclaimer, the term of this patent is extended or adjusted under 35 U.S.C. 154(b) by 0 days.

(21) Appl. No.: 09/590,202

(22) Filed: Jun. 8, 2000

(30) Foreign Application Priority Data

May 8, 1999 (IL) .................................................. 130371

(51) Int. Cl.[7] .................................................. A61B 5/08
(52) U.S. Cl. ...................................... 600/532; 600/529
(58) Field of Search .................................. 600/532, 529

(56) References Cited

U.S. PATENT DOCUMENTS

| | | |
|---|---|---|
| 4,269,194 A | 5/1981 | Rayburn |
| 4,440,177 A * | 4/1984 | Anderson .................. 128/719 |
| 4,549,553 A | 10/1985 | Hochberg |
| 4,919,037 A | 4/1990 | Mitchell |
| 4,919,144 A | 4/1990 | Vandehey |
| 4,928,687 A | 5/1990 | Lampotang |
| 4,941,476 A | 7/1990 | Fister |
| 4,947,860 A | 8/1990 | Fister |
| 5,081,998 A | 1/1992 | Yelderman et al. |
| 5,095,896 A | 3/1992 | Omoigui |
| 5,095,913 A | 3/1992 | Yelderman et al. |
| 5,130,544 A | 7/1992 | Nillsson |
| 5,156,159 A | 10/1992 | Lampotang et al. |
| 5,197,481 A | 3/1993 | Fisher |
| 5,247,185 A | 9/1993 | Herrera et al. |
| 5,261,415 A | 11/1993 | Dussault |
| 5,281,817 A | 1/1994 | Yelderman et al. |
| 5,318,037 A | 6/1994 | Evans et al. |
| 5,331,967 A | 7/1994 | Akerson |
| 5,335,656 A | 8/1994 | Bowe et al. |
| 5,377,687 A | 1/1995 | Evans et al. |
| 5,394,873 A | 3/1995 | Kraemer et al. |
| 5,402,796 A | 4/1995 | Packer et al. |
| 5,496,349 A | 3/1996 | Campbell et al. |
| 5,598,508 A | 1/1997 | Goldman |
| 5,743,259 A | 4/1998 | Kruse et al. |
| 5,751,911 A * | 5/1998 | Goldman ..................... 395/22 |
| 5,778,874 A | 7/1998 | Maguire et al. |
| 5,800,360 A | 9/1998 | Kisner et al. |
| 5,800,361 A | 9/1998 | Rayburn |
| 5,885,248 A | 3/1999 | Denton |

OTHER PUBLICATIONS

Kalenda, Z., *Mastering IR Capnography*, Kerckebosh BV of Zeist, Netherlands, 1989, pp. 100–101, p. 176, pp. 180–181.
Oridion, "A Guide to Understanding Clinical Capnography", pp. 1–2, U.S.A.

(List continued on next page.)

Primary Examiner—Robert L. Nasser
Assistant Examiner—Patricia Mallari
(74) Attorney, Agent, or Firm—Morgan & Finnegan, L.L.P.

(57) ABSTRACT

A capnograph which performs an analysis of the breath waveforms measured by the carbon dioxide sensor, interprets the results of this analysis, and outputs to the operator diagnostic information about the respiratory status of the patient, or about the adequacy of the breathing support provided to the patient. The instrument compares a number of parameters characteristic of the waveforms of the patient's breath with an internal library of the values of those parameters expected from normal waveforms stored in its memory. These parameters may either relate to specific features of the waveform in the time domain, or may characterize spectral components of the waveform in the frequency domain. The capnographic waveform analysis may be combined with further non-invasive measurements in order to provide an indication of the deviation of the value of $EtCO_2$ from $PaCO_2$.

11 Claims, 7 Drawing Sheets

OTHER PUBLICATIONS

Hess, D.R., "Capnography", Principles and Practice of Intensive Care Monitoring, McGraw Hill, N.Y., 1998, Chapter 24, pp. 377–395.

Novametrix, "$CO_2$SMO+ Respiratory Profile Monitor", pp. 1–2, 1997.

Navametrix, "$CO_2$SMO+ Respiratory Profile Monitor—Specifications", pp. 1–3, 1997.

Novametrix, "Introducing NICO", p. 1–4, 1999, www.novametri.com.

COSMED, "K4: Metabolic Testing in Only 800 Grams", Italy, pp. 1–4, 1998.

Sweldlow, D.B. "Respiratory Gas Monitoring", Monitoring in Anesthesia, $3^{rd}$ Edition, Feb. 1993, pp. 27–49.

"After Several Deaths, Office Anesthesia Under Scrutiny," *The Holland Sentinal*, Mar. 21, 1999, pp. 1–2, vol. A10.

Novametrix, "Ventrak™: Respiratory Mechanics Mobile Workstation", pp. 1–3, 1995.

* cited by examiner

WAVEFORM INTERPRETER FOR RESPIRATORY ANALYSIS

FIELD OF THE INVENTION

The present invention relates to the field of capnography in general, and in particular to instrumentation and methods for respiratory status determination by means of analyzing and interpreting the waveforms obtained in capnographic measurements.

BACKGROUND OF THE INVENTION

Capnography, as is well known in the art, is the measurement of the level of carbon dioxide ($CO_2$) in exhaled or inhaled breath. The information obtained from a capnographic measurement is generally presented on the display of the capnograph as a series of waveforms, representing the partial pressure of $CO_2$ in the patient's exhaled breath as a function of time. The information can be displayed at a fast rate, in which case the fine detail of each breath can be evaluated, or at a slow rate, in which case the trend in the end tidal value of exhaled $CO_2$ ($EtCO_2$) can be evaluated.

Clinicians use capnography in order to assess a patient's respiratory status Respiratory arrest and shunt can be speedily diagnosed, and a whole range of other respiratory problems and conditions can be determined by the shape and trends of the waveforms. In conjunction with other measurements, pulmonary blood flow, embolism and cardiac arrest can be assessed. Capnography is considered to be a prerequisite both for safe intubation and general anesthetic, and for correct ventilation management. Furthermore, recently proposed standards will mandate the use of capnographic monitoring of patients under sedation, even in simple everyday situations such as minor cosmetic surgical procedures, or pediatric dental surgery, or pediatric sedation for the performance of imaging procedures such as MRI.

Up to now, the interpretation of capnographic waveforms has generally been performed by the respiratory specialist or the anesthetist. Such personnel have sufficient experience to be able to perform an accurate diagnosis from an inspection of the waveforms on the monitor screen of the capnograph. However, with the increased use of capnography both by medica specialists in other fields and by paramedical personnel in emergency service environments, the capnograph operator is not always able to make a safe diagnosis of the patient's respiratory condition by observing the waveform graphs. The waveforms typically have a large number of different parameters, each of which taken by itself can indicate a different condition, and combinations of which can indicate yet further different conditions. These conditions relate not only to the physiological state of the patient, but also to the correct operation and connection of respiratory support apparatus There therefore exists an important need for instrumentation which will provide diagnostic support for the capnograph operator, beyond the display of the capnographic waveforms and trends on a monitor screen.

SUMMARY OF THE INVENTION

The present invention seeks to provide a new capnographic instrument which performs an analysis of the breath waveforms measured by the carbon dioxide sensor, interprets the results of this analysis and outputs to the operator a suggested diagnosis or diagnoses of the respiratory clinical state of the patient, or advises of possible malfunctions of the ventilation equipment being used to assist the patient's breathing.

There is thus provided in accordance with a preferred embodiment of the present invention, a capnograph, which provides to the operator interpretation of the capnographic waveforms measured, in the form of diagnostic information about the respiratory status of the patient, or about the adequacy of the breathing support provided by the ventilation equipment to which the patient is attached. The instrument provides this information by comparing a number of parameters characteristic of the waveforms of the patient's breath with an internal library of the values of those parameters expected from normal waveforms stored in its memory. These parameters may either relate to specific features of the waveform in the time domain, or may characterize spectral components of the waveform in the frequency domain. The differences detected are interpreted as an indication of respiratory malfunction in the patient, or as a measure of the effectiveness of the ventilation equipment, or of the patient's connection thereto. The diagnosis suggested by the system is dependent on which of the particular parameters are deviant from the normal values, and by how much. According to a preferred embodiment of the present invention, several parameters which characterize the form, frequency and magnitude of the waveform are determined for each waveform, and the values input to the processor unit of the instrument for comparison with values of these parameters expected in normal waveforms.

In addition to the analysis of individual waveforms, any long term trend in the values of the parameters is also detected, thus providing an indication of changes occurring in the respiratory state of the patient, whether as a result of his clinical state or of the performance of the ventilation equipment to which he is attached.

There is also provided in accordance with a preferred embodiment of the present invention, a method whereby the analysis and interpretation of capnographic waveforms and waveform trends are performed to provide possible diagnoses of a patient's clinical respiratory state, or indications of the effectiveness of the patient's ventilation equipment.

A useful feature of capnographic interpretation would be the determination of the value of the arterial level of carbon dioxide ($PaCO_2$) from the measured capnographic value of $EtCO_2$. It is often assumed that the value of $PaCO_2$ is close to that of $EtCO_2$ or only a few mm. of Hg higher. In effect, this is only so for subjects in good respiratory health, with a normal perfusion/ventilation ratio of pulmonary activity. For subjects with any form of dead space ventilation, or with defective perfusion mechanisms, the two values can be widely different. Since wasted ventilation is so common among a large percentage of respiratory ailments, such as severe respiratory failure, pulmonary hypoperfusion, pulmonary thromboembolism, systemic hypoperfusion and air embolism, the need to be able to determine the true value of $PaCO_2$ from the measured value of $EtCO_2$ is of great importance. Alternative methods of determining $PaCO_2$ involve invasive procedures, such as blood gas analysis.

According to a further preferred embodiment of the present invention, there is thus provided a capnograph, which, as well as measuring the usual carbon dioxide partial pressure. In the patient's breath, simultaneously measures the partial pressure of oxygen. A high oxygen level in the patient's exhaled breath is indicative of poor perfusion. According to this embodiment of the present invention, the instrument utilizes this indication of the perfusion efficiency to provide an indication of discrepancy between the values of $EtCO_2$ obtained from the carbon dioxide capnographic values, and the value of the arterial $PaCO_2$ In addition, to the determination of oxygen utilization, the ventilated volume of gas may be used in order to estimate the discrepancy between the measured values of $EtCO_2$ and the arterial $PaCO_2$ level. A low ventilation volume, which may be indicative of a perfusion shunt condition, causes the measured values of $EtCO_2$ to be less than the values of $PaCO_2$. In accordance with a further preferred embodiment of the present invention, there is therefore provided a capnographic measurement instrument, which incorporates a measurement of the ventilated volume and provides an indication of divergence of the measured values of $EtCO_2$ from the $PaCO_2$ level. The ventilated volume measurement can be obtained from a flow meter sensor section incorporated into the instrument according to the present invention, or, according to a flatter preferred embodiment, it may be obtained from a remote measurement and incorporated into a computation of the $EtCO_2$ levels.

According to yet further preferred embodiments of the present invention, it is also possible to incorporate further diagnostic measurements in the output of the automated capnograph described hereinabove, so as to support the proposed diagnostic interpretations output by the capnograph, or, to provide the operator with more information in order to choose the correct diagnosis, where the capnograph proposes more than one possibility.

According to a further preferred embodiment of the present invention, there is thus provided a capnograph incorporating the ability of self-interpretation of the breath waveforms, which executes these functions by means of the analysis of the waveforms in the frequency domain. Such an instrument is effective in detecting conditions such as the presence of the potentially fatal near zero or zero breathing zones which occur as a result of the slow beat frequency effect observed when a patient is undergoing high frequency ventilation, and the heart rate happens to fall at a frequency close to the HFV frequency.

In addition, when processing is performed in the frequency domain, it is comparatively easy to detect the high frequency components of cardiogenic oscillations in the waveform.

In accordance with yet another preferred embodiment of the present invention, there is provided apparatus for the automatic interpretation of a waveform of a breath of a subject.

In accordance with still another preferred embodiment of the present invention, there is provided apparatus for the diagnosis of the respiratory state of a subject by computer analysis of at least one breath waveform obtained from the subject.

There is further provided in accordance with yet another preferred embodiment of the present invention, apparatus as described above and wherein the waveform is obtained from a capnographic analyzer.

In accordance with a further preferred embodiment of the present invention, there is also provided apparatus for computerized breath analysis consisting of a breath receiver in fluid communication with a subject a breathing analyzer coupled to the breath receiver and operative to analyze breathing of the subject and provide at least one output, and a respiration diagnosis generator providing an indication of the respiratory status of the subject based on at least one output of the breathing analyzer.

There is provided in accordance with yet a further preferred embodiment of the present invention apparatus for computerized breath analysis consisting of a breath receiver in fluid communication with a subject, and a breathing analyzer coupled to the breath receiver and operative to analyze breathing of the subject and to provide an indication of the difference between the end tidal carbon dioxide partial pressure and the arterial carbon dioxide partial pressure of the subject.

There is even further provided in accordance with a preferred embodiment of the present invention apparatus for computerized breath analysis consisting of a breath receiver in fluid communication with a subject, and a breathing analyzer coupled to the breath receiver and operative to analyze breathing of the subject and to provide an indication of the arterial carbon dioxide partial pressure of the subject.

Furthermore, in accordance with yet another preferred embodiment of the present invention, there is provided apparatus for computerized breath analysis as described above and also consisting of a respiration diagnosis generator providing an indication of the respiratory status of the subject based on the indication of the difference between end tidal carbon dioxide partial pressure and the arterial carbon dioxide partial pressure of the subject, There is also provided in accordance with a further preferred embodiment of the present invention apparatus for computerized breath analysis as described above and also consisting of a respiration diagnosis generator providing an indication of the respiratory status of the subject based on the indication of the arterial carbon dioxide partial pressure of the subject.

In accordance with yet another preferred embodiment of the present invention, there is provided apparatus as described above and wherein the breathing analyzer includes a capnograph.

There is further provided in accordance wit yet another preferred embodiment of the present invention apparatus as described above and wherein the breathing analyzer performs analysis of at least one breath waveform.

In accordance with still another preferred embodiment of the present invention, there is provided apparatus as described above and wherein the breathing analyzer operates in a frequency domain.

There is further provided in accordance with still another preferred embodiment of the present invention apparatus as described above and wherein the breathing analyzer analyzes changes in the frequency spectrum of the breath waveform for detecting changes in the respiratory status of the subject.

In accordance with a further preferred embodiment of the present invention, there is also provided apparatus as described above and wherein the breathing analyzer compares at least part of the breath waveform with at least one reference.

There is provided in accordance with yet a further preferred embodiment of the present invention apparatus as described above and wherein the breathing analyzer analyzes variations in at least part of the breath waveform over time for detecting changes in the respiratory status of the subject.

There is even further provided in accordance with a preferred embodiment of the present invention apparatus as described above and wherein the respiratory diagnosis generator provides an indication of the respiratory status of the subject based on a capnographic measurement and also on at least one output of at least one of a breathing flow rate measurement, a breathing volume measurement, an analysis of the amounts of at least one other gas in the breath, a pulse oximetry measurement of the pulse rate and/or of the oxygen saturation level $SpO_2$, a measurement of cardiac output, of body temperature, and an ECG measurement.

Furthermore, in accordance with yet another preferred embodiment of the present invention, there is provided apparatus for providing an indication of the respiratory state of a subject, consisting of a gas analyzer which provides at least one time-dependent waveform of the partial pressure of carbon dioxide in the breath of a subject, an input circuit for receiving a sequence of digitized signals derived from the at least one waveform, a signal processor for analyzing the at least one waveform for at least one parameter which characterizes a property of the waveform, a parameter comparator for comparing the at least one parameter with a pre-defined parameter which characterizes the same property of a waveform obtained from a normal subject, and a diagnosis generator which generates a message in accordance with the output of the parameter comparator.

In accordance with yet another preferred embodiment of the present invention, there is provided apparatus for providing an indication of the respiratory state of a subject, consisting of a gas analyzer which provides a plurality of time-sequenced waveforms of the partial pressure of carbon dioxide in the breath of a subject, an input circuit for receiving a sequence of digitized signals derived from the plurality of time-sequenced waveforms, a signal processor for analyzing the plurality of time-sequenced waveforms for determining changes with time in at least one parameter of the plurality of time-sequenced waveforms, a trend analyzing unit for comparing the changes with time in the at least one parameter of the plurality of time-sequenced waveforms, with predefined changes with time in the equivalent the at least one parameter of time-sequenced waveforms typical of patients with known respiratory deficiencies, and a diagnosis generator which generates a message in accordance with the output of the trend analyzing unit.

There is further provided in accordance with yet another preferred embodiment of the present invention apparatus as described above and wherein the respiratory deficiencies arise from deficient ventilation.

There is also provided in accordance with a further preferred embodiment of the present invention apparatus as described anywhere above and wherein the gas analyzer is a capnograph.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
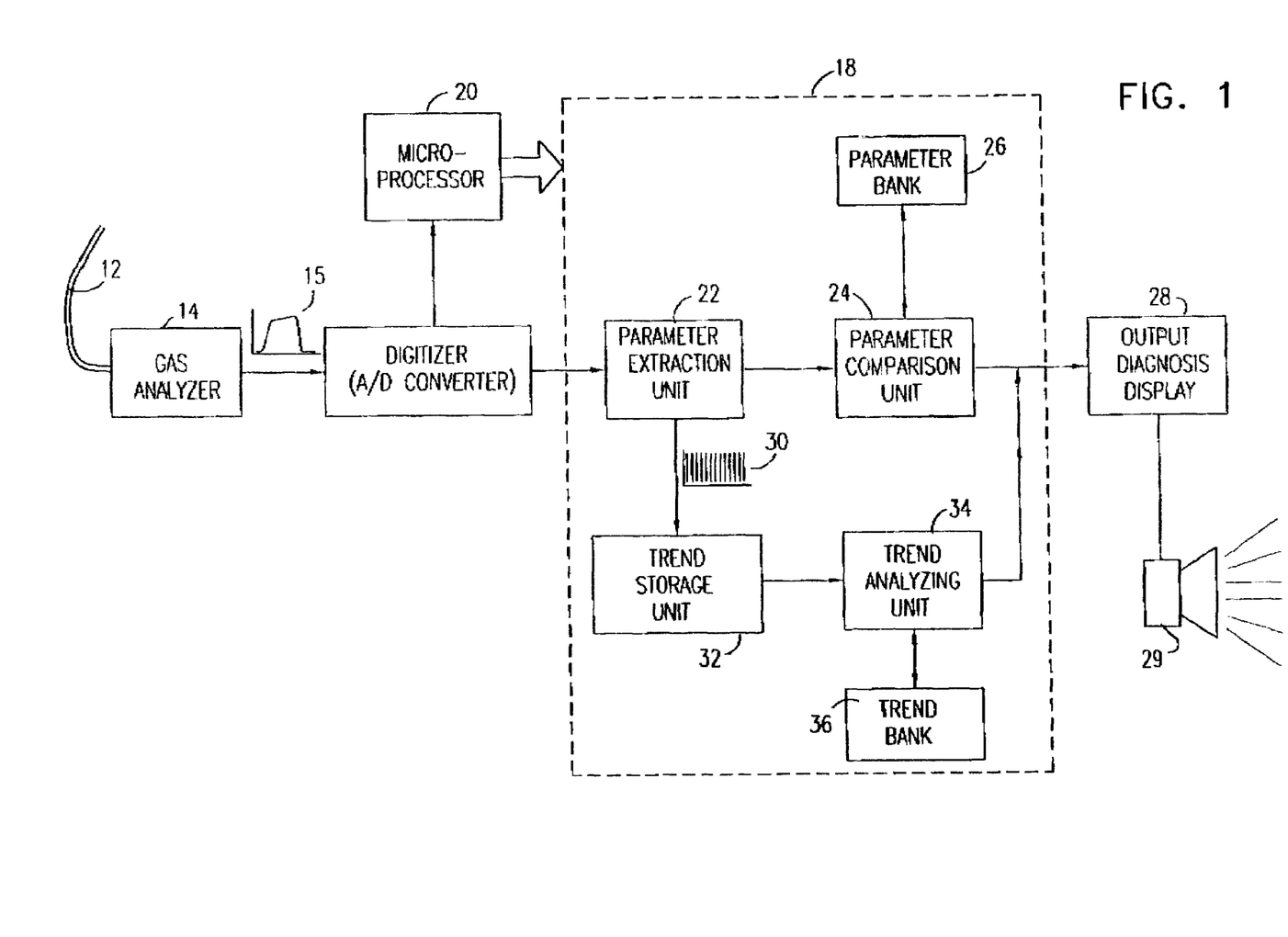
FIG. 1 is a schematic block diagram of the component parts of a capnograph capable of analyzing and interpreting breath waveforms obtained from a patient, constructed and operative according to a preferred embodiment of the present invention.

Reference is now made to FIG. 1, which is a schematic block diagram illustration of the component parts of a capnograph capable of analyzing and interpreting capnographic waveforms obtained from a subject, constructed and operative according to a preferred embodiment of the present invention. Samples of the breath of a patient are drawn by means of a sampling tube of suitable cross-section 12, into the gas analyzer section 14 of the capnograph. The gas analyzer 14, of which several different types are known in the art, analyzes the patient's breath for $CO_2$ content, and an electronic output signal is preferably generated, corresponding to the instantaneous concentration levels of $CO_2$ in waveforms 15 of successive exhaled breaths.

The analog $CO_2$ waveform signals generated by the gas analyzer section are preferably input into a digitizer 16, such as a conventional A/D converter, where the analog signals are preferably converted into a serial digital train of data for convenience in processing.

Analysis of the waveform data is performed in a signal processing unit 18. The signal processing unit 18 is preferably controlled by a general-purpose microprocessor 20, such as one of the Intel 80X88 family. The microprocessing circuit structure is of a type well known in the art, with the input data from the A/D converter received by a microprocessor bus, which communicates with the microprocessor, a random access memory (RAM), and a read-only memory (EPROM). The EPROM contains the program which controls the operation of the microprocessor according to a method of analysis, such as that preferably described below. The RAM could be, for instance, a 6264 chip, and the EPROM could be a 27C64 chip. The signal processor controls all of the waveform analyzer, diagnostic generation and display functions of the instrument.

The digital waveform signals are first input into a waveform parameter extractor 22, where the exact shape of each waveform is analyzed, and the parameters by which the waveform is characterized are preferably extracted. The parameters extracted in the waveform parameter extractor 22 are preferably stored as a matrix, which is input into a parameter comparison unit 24. Here, the matrix is preferably compared, by means of a parameter comparison method, with the parameter matrix of a typical breath waveform obtained from a normal subject, stored as a reference set in the parameter bank 26. Any anomalies detected cause the outputting of messages suggesting possible combinations of diagnoses for the particular set of parameters input. These messages are preferably displayed to an operator on an output diagnosis display device 28.

In addition to outputting a matrix of all of the extracted waveform parameters of a single waveform, for comparison with the single waveform of a normal subject, the waveform parameter extraction unit 22 also preferably outputs a continuous data stream corresponding to the parameters obtained from a sequence of breath waveforms. The serial values of these parameters are preferably input into a storage unit 32, and on demand, into a trend analyzing unit 34 where any long term trend is detected in the value of any of the parameters selected. Any long term trend is compared in the trend analyzing unit 34 with predetermined trends stored in the trend bank 36, these predetermined trends representing abnormal clinical or equipment conditions. The establishment of any abnormality in the observed trend results in the outputting of an informative message to the operator on the output diagnosis display device 28. The capnograph may also be preferably programmed so that certain diagnostic respiratory conditions, which could indicate the onset of what is regarded by presently accepted medical practice as an emergency situation also actuate an audible or visible alarm 29.

Figure 2A:
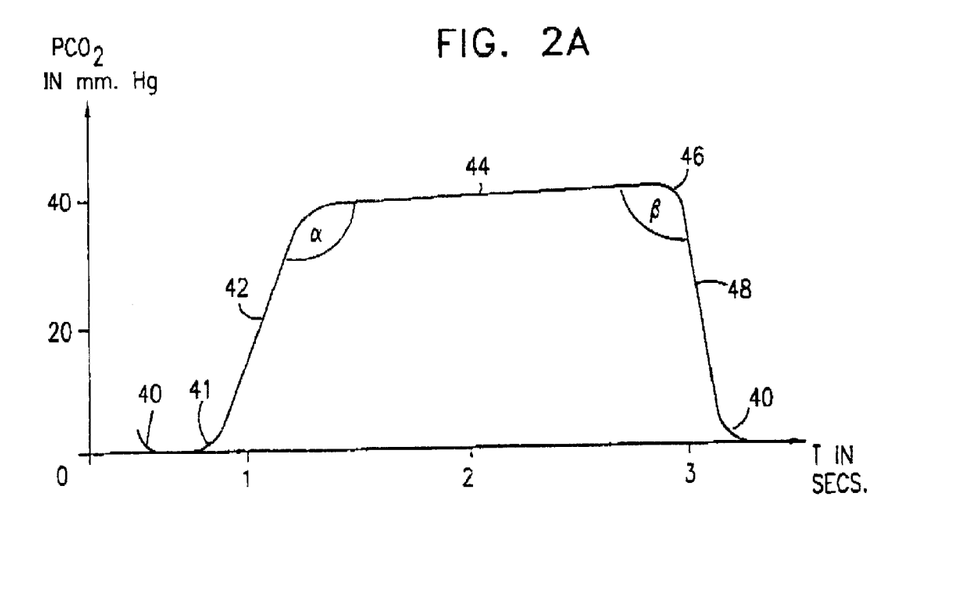
FIG. 2A is a graphical illustration of a waveform of a normal capnograph plotted at high speed, with characteristic features marked thereon.

Reference is now made to FIG. 2A which is an illustration of a typical capnogram waveform obtained from a normal healthy subject, recorded at high speed to show its detail and constituent parts. During inspiration the baseline 40 shows a close-to-zero value of the partial pressure of carbon dioxide, $PCO_2$, unless partial rebreathing is present. Even at the commencement of exhalation 41, $PCO_2$ remains close to zero as gas from the anatomical dead space leaves the airway. The capnogram then rises sharply 42 as alveolar gas mixes with dead space gas, until the alveolar plateau 44 is reached. The alveolar plateau 44 is maintained till the end of the exhalation phase 46, with the value of $PCO_2$ rising gradually during the whole of the plateau, up to the end tidal value, $EtCO_2$. This occurs at the onset of the inhalation phase, during which the value of $PCO_2$ shows a sharp fall 48 back to its virtually zero value 40. The close-to-zero value of $PCO_2$ at the end of the inspiration phase is known as the final inspired value $FiCO_2$.

The angle between tie alveolar rise 42 and the alveolar plateau 44 is known as the alpha angle α, and is normally in a range between approximately 100° and approximately 110°. The angle α is determined primarily by the V/Q (ventilation/perfusion) status of the lungs, as is well known in the art. Patients with obstructions of the airway, such as in the, case of chronic obstructive pulmonary disease (COPD) or asthma, have an increased alpha angle. The alpha angle is thus a widely used parameter for a first hand assessment of the patient's overall pulmonary state.

An alternative parameter which can be used for determining the general pulmonary state of the patient is the overall rate of rise of $PCO_2$ This is determined by dividing the maximum value of $PCO_2$ achieved in the waveform, by the time taken from the start of exhalation to the achievement of the maximum value of $PCO_2$. In order to avoid end effects, the 10% and 90% points of the values of $PCO_2$ are typically used for the calculation.

The nearly 90° angle between the alveolar plateau 44 and the descending limb 48 of the capnogram is known as the beta angle β. The beta angle increases as the degree of rebreathing increases. The various parts of the waveform are known as the phases of the waveform, the alveolar rise phase I, the alveolar plateau phase II, and the inhalation descent, phase III, as is well known in the art.

Figure 2B:
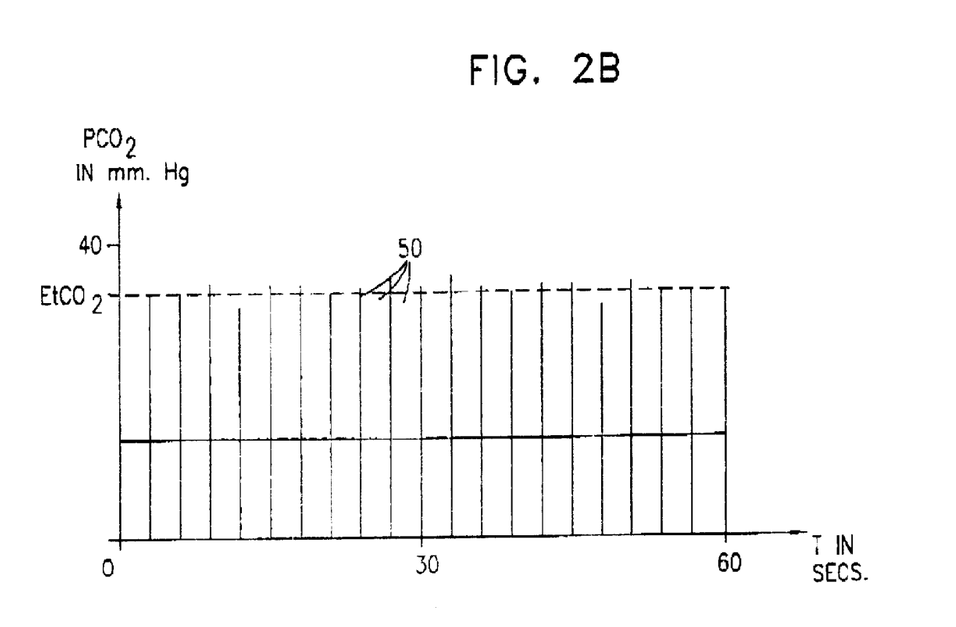
FIG. 2B is a graphical illustration of a series of waveforms taken from a normal patient, plotted at low speed, showing an essentially constant value of $EtCO_2$, as expected from the capnograph of a normal patient.

FIG. 2B is a trace of the value of $PCO_2$, plotted at low speed over a large number of breaths to determine any long term trend present. In general, because of the slow speed of the scan rate, the only relevant features typically seen from such a plot are the values of $EtCO_2$, which are shown in FIG. 28 as the peaks 50 of the successive waveforms plotted. As expected from the capnogram of a normal patient, FIG. 2B shows an essentially constant long term value of $EtCO_2$.

The long term plot of $EtCO_2$ in particular, as shown in FIG. 2B, is commonly used in the art for long term respiratory assessment since $EtCO_2$ is the standard long term trace generally displayed on the monitor screen of an analog recording capnograph. For this reason, in the preferred embodiments and examples described in this specification, the value of $EtCO_2$ is chosen as the a parameter inspected for long term trends. It is appreciated, though, that since capnographs according to the present invention, perform digital signal processing on the waveforms, the parameter $EtCO_2$ has no more preference for use than any of the other selected parameters by which the waveform is characterized.

The shape of the normal waveform illustrated in FIG. 2A, and the levels of $EtCO_2$ plotted in FIG. 2B, enable a set of parameters to be chosen which characterize the waveforms, and enable quantitative comparisons to be made with abnormal waveforms.

According to one preferred embodiment of the present invention, the parameters used for analysis are as follows:

the alpha angle, α;

the beta angle, β;

the end tidal level $EtCO_2$;

the final inspired value $FiCO_2$;

the breath rate, f, in breaths per minute; and the overall rate of rise of $PCO_2$, R.

It is appreciated that not all of the set of parameters described above need necessarily be used for each diagnosis, or for each programmed procedure used by the system to achieve the required diagnoses. Different preferred embodiments of the present invention may use some or all of the above-described parameters.

It is also appreciated that the set of parameters described above comprises only one of several possibilities for characterizing capnographic waveforms. The present invention is not therefore limited to the preferred embodiment described herein using this defined set of parameters, but could equally well be implemented with different parameters.

Figure 3A:
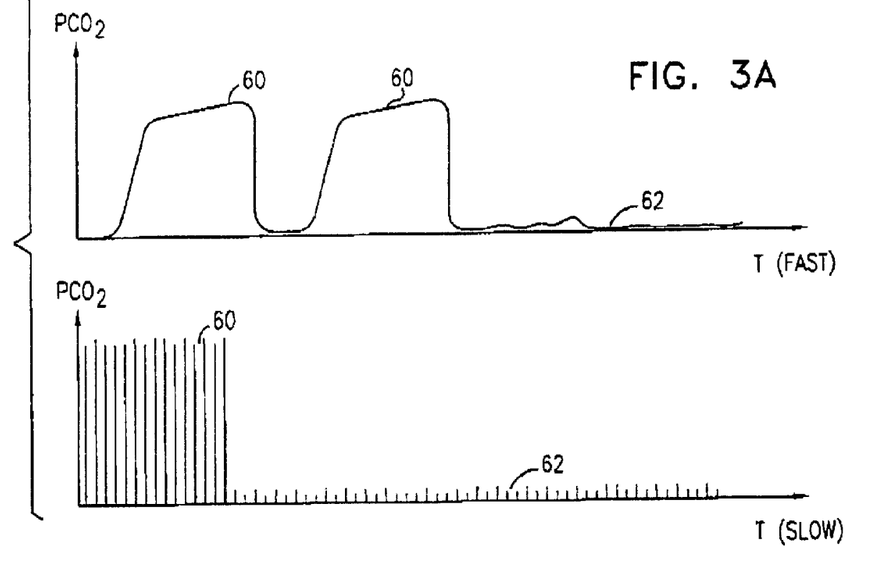
FIGS. 3A and 3B are examples of typical capnographic waveforms and their long term change trends obtained from patients having various clinical respiratory problems, or arising from various ventilation equipment malfunctions. Each figure includes a fist recording showing a single waveform or a small number of waveforms, and in addition, a slow plot showing the long-term trend.
Figure 3B:
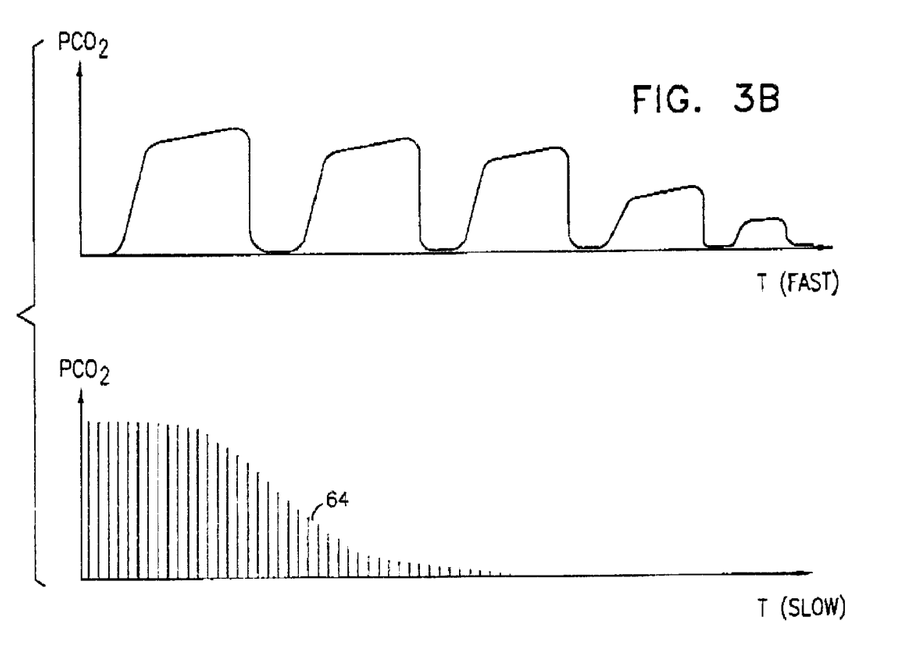

Reference is now made to FIGS. 3A and 3B, which are illustrations of typical examples of capnographic waveforms and their long term change trends, similar to those, which would be obtained from patients having various clinical respiratory states or from patients connected to ventilation equipment with various malfunctions. These abnormal capnograms are now discussed to illustrate the method used in the present invention to analyze the various aspects of the capnograph waveforms and long term trends, As previously mentioned, the examples of the long term trend plots use the parameter $EtCO_2$ to illustrate the effect of the various conditions described, but it is appreciated that any other suitable parameter could also be used according to other preferred embodiments of the present invention.

FIG. 3A shows fast and slow speed capnograms displaying normal waveforms 60, followed by a sudden loss of $EtCO_2$ to zero or near zero values 62. This may be indicative of the total disconnection of the airway, or of a dislodged or obstructed endotracheal (ET) tube, or of esophageal intubation, or of complete ventilator malfunction.

FIG. 3B shows a capnogram with an exponential decrease 64 in the value of $EtCO_2$. This may be symptomatic of cardiopulmonary arrest, or of a pulmonary embolism, or a sudden massive blood loss, or of a cardiopulmonary bypass.

It is appreciated that the capnograms shown in FIGS. 3A and 3B are only examples of common anomalies found in capnographic recordings from patients in various clinical states, and that it is not to be inferred that the present invention is able to recognize and diagnose the causes of these anomalies only. It is believed that the capnograph according to the present invention can be programmed to diagnose any conditions for which preliminary analysis of the resulting waveforms has been performed. Examples of more of such conditions can be found in several standard works on the subject of clinical capnography, such as the book entitled "Mastering Infra-red Capnography" by Z. Kalenda, published by Kerckebosch B V, of Zeist, Netherlands (1989), or in the pamphlet entitled "A Guide to Understanding Clinical Capnography" published by Oridion Medical, both of which are hereby incorporated by reference, each in their entirety.

Figure 4:
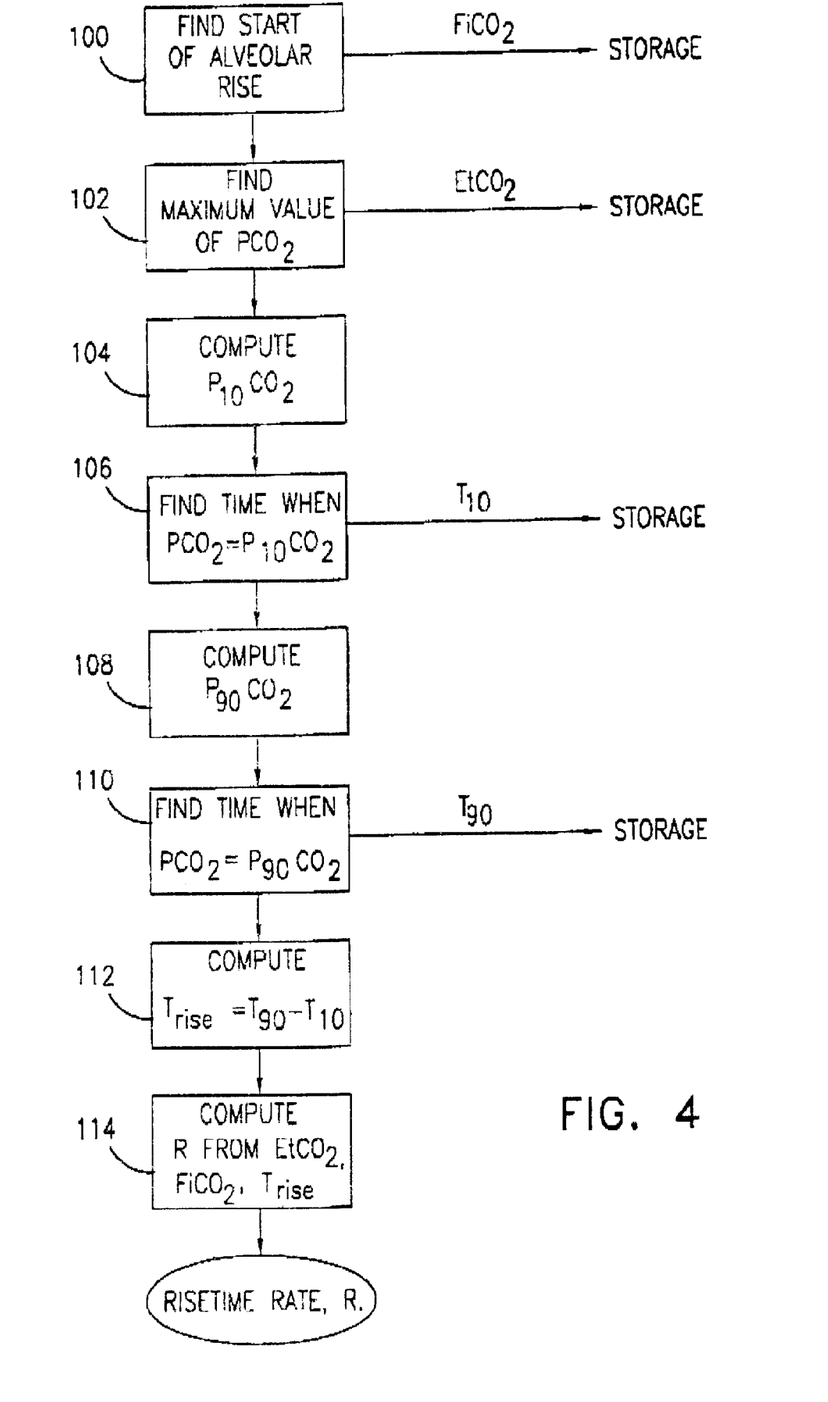
FIG. 4 is a simplified flow chart illustration of a preferred embodiment of a parameter handling method which operates within the waveform parameter extraction unit of FIG. 1.

Reference is now made to FIG. 4 which is a simplified flow chart illustration of a preferred embodiment of a parameter handling method which operates within the waveform parameter extraction unit 22 shown in FIG. 1. The function of the parameter handling method described is to analyze the breath waveforms, and to extract therefrom, R, the rate of rise parameter. The method operates on an input signal which corresponds to the instantaneous value of the carbon dioxide partial pressure $PCO_2$.

In step 100, the commencement of the alveolar rise is determined by detecting when the signal begins to rise above its threshold level. This threshold level of the carbon dioxide partial pressure is stored in memory as $FiCO_2$.

In step 102, the end of the rise in carbon dioxide partial pressure Is determined by detecting when the value of $PCO_2$ reaches a maximum. This carbon dioxide partial pressure is stored in memory as $EtCO_2$.

In step 104, a computation is made of the carbon dioxide partial pressure:

$$P_{10\%}CO_2 = FiCO_2 + 0.1(EtCO_2 - FiCO_2)$$

In step 106, the time $T_{10\%}$ is determined at which the carbon dioxide partial pressure in the waveform is equal to $P_{10\%}CO_2$.

In step 108, a computation is made of the carbon dioxide partial pressure:

$$P_{90\%}CO_2 = FiCO_2 + 0.9(EtCO_2 - FiCO_2)$$

In step 110, the time $T_{90\%}$ is determined at which the carbon dioxide partial pressure in the waveform is equal to $P_{90\%}CO_2$.

In step 112, the time $T_{rise}$ is computed from the difference $T_{90\%} + T_{10\%}$ In step 114, the rise time rate R, is computed by the expression:

$$R = (EtCO_2 - FiCO_2)/(T_{90\%} - T_{10\%})$$

The outcome of steps 100 to 114 is that the R parameter, used for defining the overall respiratory state of a patient, is obtained from the waveform. This parameter is then entered into the parameter comparator 24 shown in FIG. 1.

The parameter comparator 24 compares the parameters extracted from the recorded waveform with the reference parameters stored in the parameter bank 26. The method of comparison is performed by means of well known methods of digital matrix correlation.

It is to be understood that the flow chart described above for calculating the value of the rate of rise parameter R, is only one preferred example for calculating a parameter useful for obtaining diagnostic information from capnographic waveforms. It is to be understood that the present invention is not limited to the preferred embodiment described herein for calculating this parameter, but could equally well be implemented for calculating other diagnostically useful parameters.

Figure 5:
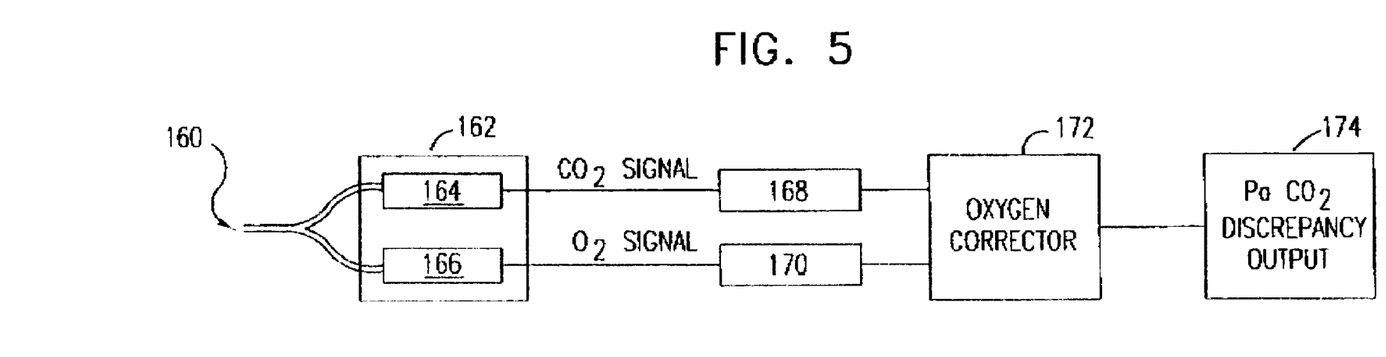
FIG. 5 is a simplified block diagram of a capnograph according to another preferred embodiment of the present invention, which simultaneously measures the partial pressure of oxygen and of carbon dioxide in a subject's breath.

Reference is now made to FIG. 5, which is a simplified block diagram of a capnographic waveform interpreter, according to yet another preferred embodiment of the present invention. This capnograph, as well as measuring the usual carbon dioxide partial pressure in the patient's breath, simultaneously measures the partial pressure of oxygen. This capnograph is called an arterial $CO_2$ estimation capnograph, because of its ability to provide an indication of the discrepancy between the values of $EtCO_2$ and $PaCO_2$. This estimation can be made without the need for any invasive procedures.

The breath 160 of the patient is sampled into the gas analyzer section 162 of the capnograph, which contains two separate analyzing channels, a carbon dioxide analyzer 164, and an oxygen analyzer 166. The respiratory waveform analysis units, 168 and 170, of the carbon dioxide and oxygen waveforms respectively, provide output data including values of inspired and expired $PCO_2$ and $PO_2$, the carbon dioxide and oxygen partial pressures respectively, in the patient's breaths. The values of $PO_2$ are converted in computational unit 172 into an oxygen correction factor which is applied to the value of $EtCO_2$ measured, and the result gives an indication on the output unit 174, of the discrepancy between the values of $EtCO_2$ and $PaCO_2$. The correction factor itself is a function of the difference between inspired and expired $PO_2$ levels, in that the smaller the difference, the greater is the perfusion degradation effect present in the patient's pulmonary system, and the larger the estimated discrepancy between the measured value of $EtCO_2$ and the value of the patients $PaCO_2$.

Figure 6:
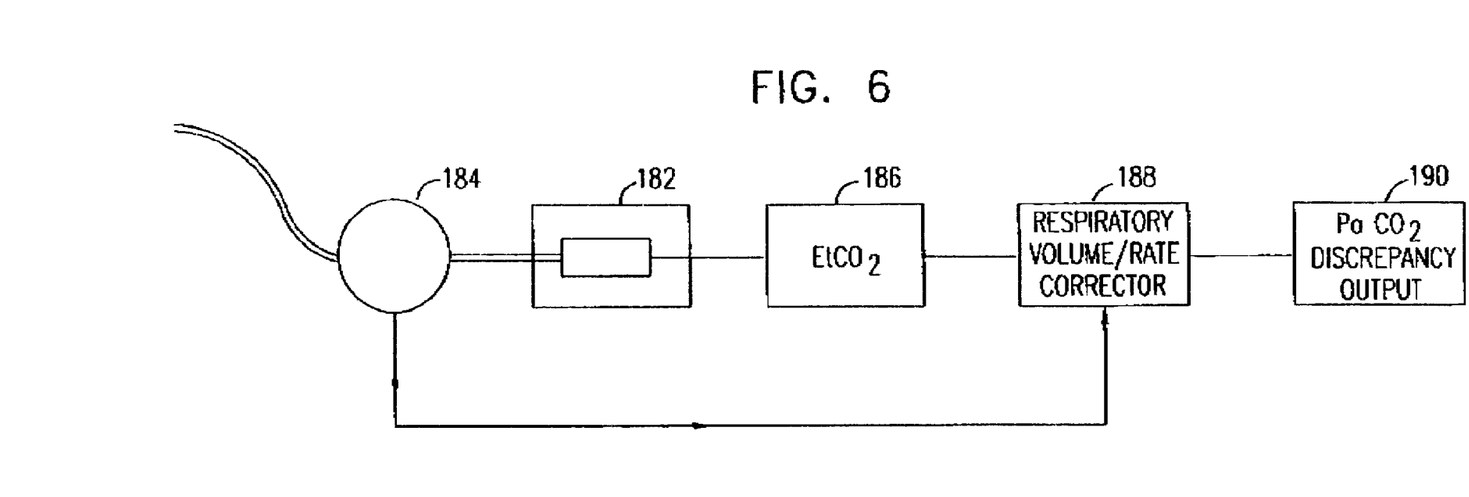
FIG. 6 is a simplified block diagram of a capnograph according to another preferred embodiment of the present invention, which as well as measuring the carbon dioxide partial pressure in a subject's breath, simultaneously inputs the result of a pulmonary ventilation measurement.

Reference is now made to FIG. 6, which is a simplified block diagram of a capnograph according to yet another preferred embodiment of the present invention. The patient's pulmonary ventilation is measured on a pulmonary volume meter 184. The carbon dioxide partial pressure in the patient's breath is measured in a gas analyzer 182. The value of $EtCO_2$ measured in the capnograph unit 186 has a correction factor applied to it 188 according to the respiratory volume measured, and the result is output to the display unit 190 as an estimation of the discrepancy between the measured value of $EtCO_2$ and the value of the patient's $PaCO_2$.

According to another preferred embodiment of the present invention, the pulmonary volume meter 184 shown in FIG. 6, may alternatively or additionally provide data about the breathing flow rate for inputting to the respiratory volume/rate corrector unit 188, in order to correct the values of $EtCO_2$ measured in the capnograph unit 186.

Figure 7:
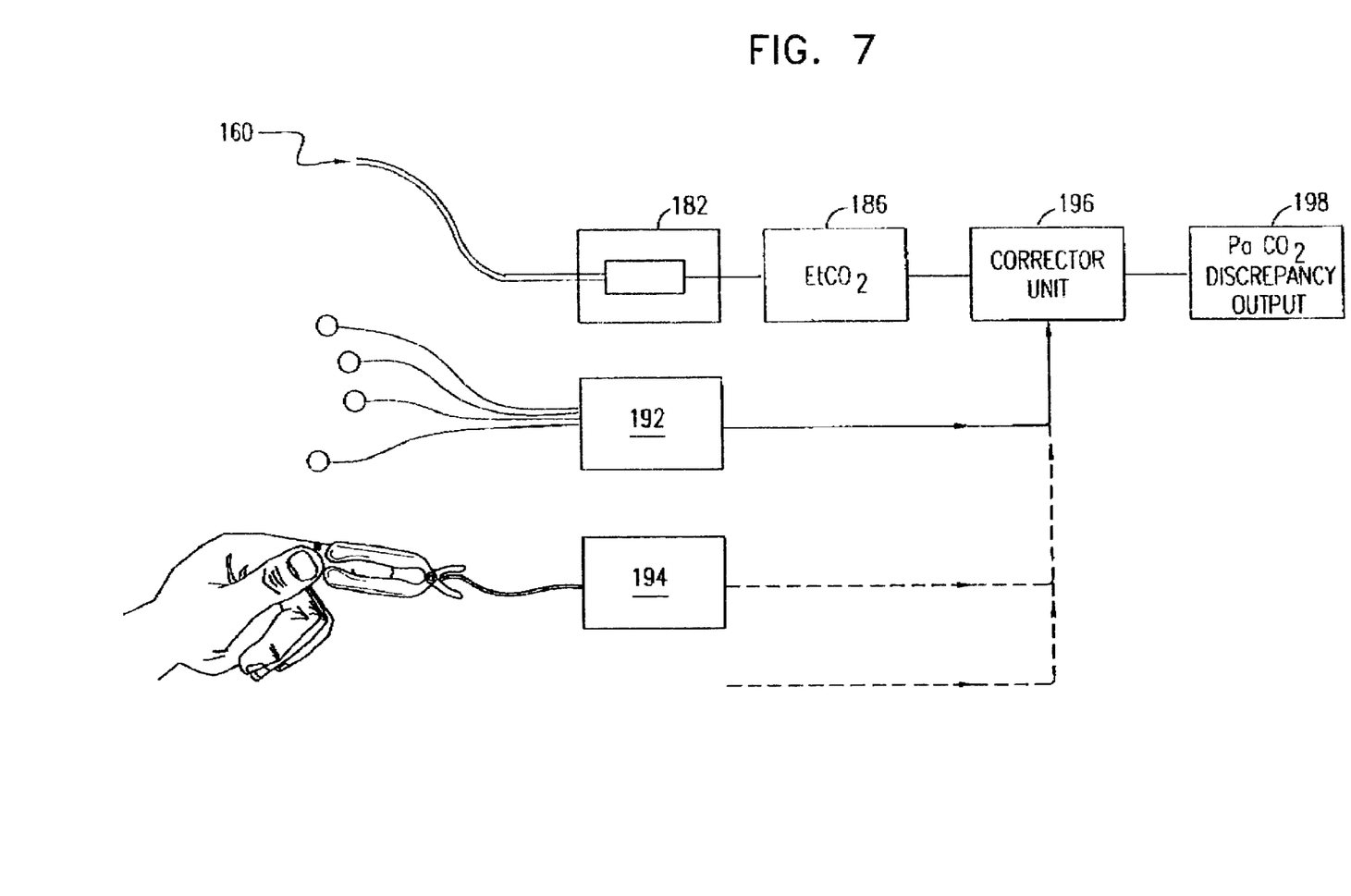
FIG. 7 is a simplified block diagram of a capnograph according to another preferred embodiment of the present invention, which as well as measuring the carbon dioxide partial pressure in a subject's breath, simultaneously inputs the result of an ECG measurement, or the result of a pulse oximetry measurement, or another suitable measurement, such as a measurement of cardiac output.

Reference is now made to FIG. 7, which is a simplified block diagram of a capnograph according to yet another preferred embodiment of the present a invention, which combines parameters from non-respiratory measurements to make a diagnostic determination of the respiratory state of the patient. The breath 160 of the patient is sampled into a gas analyzer 182, where the carbon dioxide partial pressure is measured. In common with the embodiments shown in FIGS. 5 and 6, the value of waveform output parameters, such as $EtCO_2$, is extracted from the measured waveforms by means of a capnographic interpreter unit 186. In addition to the capnographic measurements other measurements are made on the patient, and the output from these measurements are applied in the corrector unit 196, as correction factors to the measured values of, for example, $EtCO_2$. Examples of non-respiratory measurements which may be used in this embodiment are any of those which may provide information about the condition of the blood circulation, or its content, such that this data may be used to correlate with the transfer in the lungs, of arterial carbon dioxide from the blood to the patient's exhaled breath. According to various preferred embodiments, such non-respiratory measurements could include ECG or simple pulse rate measurements 192, pulse oximetric measurement 194 of tie arterial oxygen saturation level $SpO_2$ and/or of the pulse rate, a measurement of cardiac output, or a body temperature measurement. Any of these measurements, alone or in combination, can be combined with the output data from the capnographic waveform interpreter to provide informative information about, for instance, the expected deviation of $EtCO_2$ from the value of $PaCO_2$. The corrected arterial carbon dioxide partial pressure $PaCO_2$ is output in the display unit 198.

Figure 8:
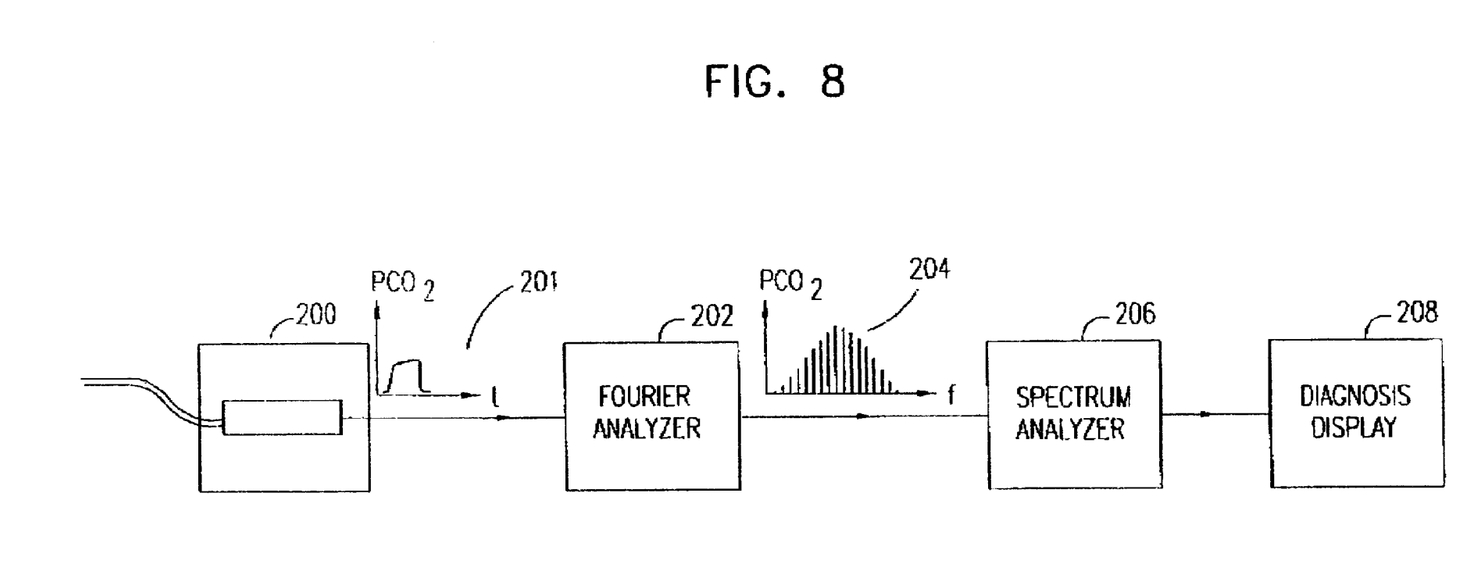
FIG. 8 is a simplified block diagram of a capnograph according to yet another preferred embodiment of the present invention, which analyzes a subject's breath waveforms in the frequency domain.

Reference is now made to FIG. 8, which is a simplified block diagram of a capnograph according to yet another preferred embodiment of the present invention, which analyzes the breath waveforms in the frequency domain. The carbon dioxide partial pressure in the patient's breath is measured in the gas analyzer section 200. The time varying output signals 201 from tie gas analyzer are input into a Fourier analyzer circuit 202, which extracts the Fourier components 204 of the waveform. The frequency spectrum analyzer 206 then searches the Fourier frequency components of the waveforms for anomalous signs associated with abnormal respiratory function. Any such signs cause a diagnostic message to be generated and displayed on the display unit 208.

According to a preferred embodiment of the present invention, which analyzes the breath waveforms in the frequency domain, the frequency spectrum analyzer searches for unrelated frequency content in the waveform. If two uncorrelated base frequencies are detected, with widely differing frequencies, according to normal physiological findings, the lower frequency should be attributed to the respiration rate, and the higher frequency to heart beat. The capnographic comparisons to detect respiratory abnormalities, should be performed on frequency components correlated to the respiratory rate only. Any higher frequency components are attributed to cardiogenic oscillations.

This embodiment is particularly useful for monitoring patients undergoing high frequency ventilation. In analyzing the frequency components, the existence of a very low beat frequency may be indicative of the presence of a zero or near-zero breathing zone. The instrument is then programmed to issue a warning to the attending medical staff to move the ventilating frequency away from its present value.

It will be appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. Apparatus for computerized breath analysis comprising:

a breath receiver in fluid communication with a subject;

a breathing analyzer coupled to the breath receiver and operative to analyze a plurality of sequential breath waveforms of said subject and provide at least one output; and a respiration diagnosis generator utilizing said at least one output of said breathing analyzer to provide an indication of the respiratory status of the subject based on a relationship between multiple ones of said plurality of breath waveforms.

2. Apparatus according to claim 1 and wherein said breathing analyzer includes a capnograph.

3. Apparatus according to claim 1 and wherein said breathing analyzer compares a plurality of said sequential breath waveforms with at least one reference.

4. Apparatus according to claim 1 and wherein said breathing analyzer analyzes variations in said plurality of breath waveforms over time for detecting changes in said respiratory status of said subject.

5. Apparatus according to claim 4 and also comprising a trend analyzing unit for comparing said variations over time in said plurality of waveforms with predefined variations over time in time-sequenced waveforms typical of patients with known respiratory deficiencies.

6. Apparatus for providing an indication of the clinical respiratory state of a subject, comprising:

a gas analyzer which provides a plurality of sequential waveforms of the partial pressure of the breath of a subject;

a signal processor for analyzing said plurality of sequential waveforms for at least one parameter which characterizes a property of said waveforms;

a parameter comparator for comparing values of said at least one parameter with a predefined parameter which characterizes the same property of a waveform obtained from a normal subject; and a diagnosis generator which generates a response in accordance with the changes in the output of said parameter comparator.

7. Apparatus according to claim 6 and wherein said gas analyzer is a capnograph.

8. Apparatus for providing an indication of the respiratory state of a subject, comprising:

a gas analyzer which provides a plurality of time-sequenced waveforms of the breath of a subject;

an input circuit for receiving a sequence of digitized signals derived from said plurality of time-sequenced waveforms;

a signal processor for analyzing said sequence of digitized signals for determining changes with time in at least one parameter of said plurality of time-sequenced waveforms;

a trend analyzing unit for comparing said changes with time in said at least one parameter of said plurality of time-sequenced waveforms, with predefined changes with time in the equivalent said at least one parameter of time-sequenced waveforms typical of patients with known respiratory deficiencies; and a diagnosis generator which generates a message in accordance with the output of said trend analyzing unit.

9. Apparatus according to claim 8 and wherein said gas analyzer is a capnograph.

10. Apparatus for computerized breath analysis comprising:

a breath receiver in fluid communication with a subject;

a breathing analyzer coupled to the breath receiver and comprising a waveform parameter extractor operative to analyze a first and a second breath waveform of said subject and provide at least one output depending on differences between said first and said second breath waveforms; and a respiration diagnosis generator providing an indication of the respiratory status of said subject based on said at least one output of said breathing analyzer.

11. Apparatus according to claim 10 and wherein said at least one output depending on differences between said first and said second breath waveforms is processed by a trend analyzer, operative to compare said at least one output, with predefined changes with time in time-sequenced waveforms typical of patients with known respiratory deficiencies.

* * * * *

UNITED STATES PATENT AND TRADEMARK OFFICE
CERTIFICATE OF CORRECTION

PATENT NO.     : 6,428,483 B1
DATED          : August 6, 2002
INVENTOR(S)    : Carlebach et al.

It is certified that error appears in the above-identified patent and that said Letters Patent is hereby corrected as shown below:

<u>Title page,</u>
Item [75], Inventors, please add: -- Baruch Shlomo Krauss, Brookline, MA (US) -- as a joint inventor.

Signed and Sealed this

Eighth Day of June, 2004

JON W. DUDAS
*Acting Director of the United States Patent and Trademark Office*